(12) United States Patent
Hobbs et al.

(10) Patent No.: US 7,163,533 B2
(45) Date of Patent: Jan. 16, 2007

(54) VASCULAR TREATMENT DEVICE AND METHOD

(75) Inventors: Eamonn Hobbs, Queensbury, NY (US); William M. Appling, Granville, NY (US)

(73) Assignee: AngioDynamics, Inc., Queensbury, NY (US)

( * ) Notice: Subject to any disclaimer, the term of this patent is extended or adjusted under 35 U.S.C. 154(b) by 171 days.

(21) Appl. No.: 10/393,922

(22) Filed: Mar. 20, 2003

(65) Prior Publication Data

US 2003/0191460 A1 Oct. 9, 2003

Related U.S. Application Data

(60) Provisional application No. 60/370,050, filed on Apr. 4, 2002.

(51) Int. Cl.
*A61B 18/18* (2006.01)
*A61B 18/20* (2006.01)

(52) U.S. Cl. ............... 606/11; 606/7; 606/15; 606/41; 606/46

(58) Field of Classification Search .......... 606/7, 606/11–18, 41, 46, 47, 40; 604/14
See application file for complete search history.

(56) References Cited

U.S. PATENT DOCUMENTS

| 5,250,034 | A | 10/1993 | Appling et al. |
| 5,330,467 | A | 7/1994 | Abela et al. |
| 5,417,653 | A * | 5/1995 | Sahota et al. ............... 604/20 |
| 5,458,568 | A * | 10/1995 | Racchini et al. ............ 604/19 |
| 5,458,596 | A * | 10/1995 | Lax et al. .................... 606/41 |
| 5,575,787 | A | 11/1996 | Abela et al. |
| 5,925,016 | A * | 7/1999 | Chornenky et al. ......... 604/19 |
| 5,999,678 | A | 12/1999 | Murphy et al. |
| 6,165,172 | A * | 12/2000 | Farley et al. ................ 606/40 |
| 6,179,832 | B1 * | 1/2001 | Jones et al. ................. 606/41 |
| 6,330,473 | B1 * | 12/2001 | Swanson et al. ............ 604/21 |
| 2002/0007181 | A1 | 1/2002 | Zikorus et al. |

* cited by examiner

*Primary Examiner*—David M. Shay
(74) *Attorney, Agent, or Firm*—Reed Smith LLP; Harry K. Ahn

(57) ABSTRACT

A catheter device for treating a vascular disease is provided. The catheter device includes an energy delivery device such as an optical fiber for delivering laser energy and a catheter. The catheter lumen receives the optical fiber and a fluid such as an anesthetic agent or vasoconstricting agent. According to the invention, a plurality of exits are formed in the sidewall of the catheter. The exits are in communication with the catheter lumen and administer the fluid into the blood vessel. By administering the fluid from within the catheter lumen, the present catheter device eliminates the need to make numerous external punctures to deliver fluid injections.

29 Claims, 7 Drawing Sheets

VASCULAR TREATMENT DEVICE AND METHOD

CROSS-REFERENCE TO RELATED APPLICATIONS

This application claims priority to U.S. Provisional Application No. 60/370,050, filed Apr. 4, 2002, which is incorporated herein by reference.

FIELD OF THE INVENTION

The present invention relates to a medical device for treatment of vascular diseases, and more particularly, to a device for treating varicose veins using an endovascular laser optical fiber and catheter.

BACKGROUND OF THE INVENTION

Veins are thin-walled and contain one-way valves that control blood flow. Normally, the valves open to allow blood to flow into the deeper veins and close to prevent back-flow into the superficial veins. When the valves are malfunctioning or only partially functioning, however, they no longer prevent the back-flow of blood into the superficial veins. As a result, venous pressure builds at the site of the faulty valves. Because the veins are thin walled and not able to withstand the increased pressure, they become what are known as varicose veins which are veins that are dilated, tortuous or engorged.

In particular, varicose veins of the lower extremities is one of the most common medical conditions of the adult population. It is estimated that varicose veins affect approximately 25% of adult females and 10% of males. Symptoms include discomfort, aching of the legs, itching, cosmetic deformities, and swelling. If left untreated, varicose veins may cause medical complications such as bleeding, phlebitis, ulcerations, thrombi and lipodermatosclerosis.

Traditional treatments for varicosities include both temporary and permanent techniques. Temporary treatments involve use of compression stockings and elevation of the diseased extremities. While providing temporary relief of symptoms, these techniques do not correct the underlying cause, that is the faulty valves. Permanent treatments include surgical excision of the diseased segments, ambulatory phlebectomy, and occlusion of the vein through chemical or thermal means.

Surgical excision requires general anesthesia and a long recovery period. Even with its high clinical success rate, surgical excision is rapidly becoming an outmoded technique due to the high costs of treatment and complication risks from surgery. Ambulatory phlebectomy involves avulsion of the varicose vein segment using multiple stab incisions through the skin. The procedure is done on an outpatient basis, but is still relatively expensive due to the length of time required to perform the procedure.

Chemical occlusion, also known as sclerotherapy, is an in-office procedure involving the injection of an irritant chemical into the vein. The chemical acts upon the inner lining of the vein walls causing them to occlude and block blood flow. Although a popular treatment option, complications can be severe including skin ulceration, anaphylactic reactions and permanent skin staining. Another disadvantage is that treatment is limited to veins of a particular size range. In addition, there is a relatively high recurrence rate due to vessel recanalization.

Endovascular thermal energy therapy is a relatively new treatment technique for venous reflux diseases. With this technique, thermal energy in the form of laser or radio frequency (RF) energy is delivered by an energy delivery device that is percutaneously inserted into the diseased vein prior to energy delivery. In a laser therapy, an optical fiber is used as the energy delivery device whereas in an RF therapy, RF electrodes are used as the energy delivery device. The procedure for the thermal energy therapy involves inserting an introducer catheter or sheath and advancing it to within a few centimeters of the saphenofemoral junction of the greater saphenous vein. In the case of laser therapy, once the introducer catheter is properly positioned, a flexible optical fiber is inserted into the lumen of the catheter or sheath and advanced until the distal fiber tip is near the catheter tip but still protected within the catheter lumen.

Once the catheter and flexible optical fiber are positioned within the vein, the tissue immediately surrounding the diseased vessel segment is subjected to numerous needle punctures to make percutaneous injections of a tumescent anesthetic agent. The injections, typically lidocaine with or without epinephrine, are administered under ultrasonic guidance along the entire length of the greater saphenous vein into the perivenous space. The tumescent injections perform several functions. First, the anesthetic injection inhibits pain caused from the application of energy to the vein. Second, the injection causes the vein to spasm which reduces the diameter of the vein and brings the vessel wall in close proximity to the catheter and the optical fiber. The constricted vessel diameter facilitates efficient energy transmission to the vessel wall through the optical fiber when the laser energy is applied. Third, the tumescent injection also provides a barrier between the vessel and the adjacent tissue and nerve structures, which restricts the heat damage to only the vessel itself and prevents non-target tissue damage.

After the anesthetic injections are made through multiple puncture sites, the catheter is withdrawn approximately 1–3 centimeters while the optical fiber is held steady to expose the distal tip of the optical fiber. A laser generator is then activated to cause laser energy to be emitted from the bare flat tip of the fiber into the constricted vessel. The thermal energy from the laser contacts the blood causing hot bubbles of gas to be created. The gas bubbles transfer thermal energy to the vein wall, causing cell necrosis and eventual vein collapse. With the laser generator turned on, the fiber and catheter are slowly withdrawn as a single unit until the entire diseased segment of the vessel has been treated. The damaged vessel becomes occluded, collapses and can no longer support blood flow.

For such endovascular laser treatment, the injection of tumescent anesthesia through multiple punctures along the diseased segment is considered a standard and necessary step in the treatment protocol. However, there are several disadvantages associated with such a conventional method of administering local anesthesia injections. The anesthetic injection process is cumbersome and is the most time-consuming step in the treatment procedure because of the number of punctures that has to be made. Typically, injections are administered along the entire length of the greater saphenous vein in 2–3 cm increments. The total injection length varies but is usually between 30 and 40 cm.

Accordingly, approximately 10 to 20 injections, and therefore 10 to 20 punctures, are required before the laser treatment can begin.

In addition to the time required to administer multiple injections, peri-venous injections are disadvantageous because they are painful to the patient, leave puncture wounds, and may increase bruising and post-procedure complications because of the way the injection is administered. Each injection is administered under ultrasound guidance due to the necessity of accurately positioning the needle between the fascia and vein. The physician will often use the catheter as a target when inserting the needle into the patient's tissue. In some cases, a physician may inadvertently puncture the vein and even the catheter wall when positioning the needle. When this occurs, the vein wall may be lacerated resulting in excessive bruising and patient discomfort. Lacerations of the vein wall may also result in non-targeted thermal damage outside of the vessel as the gas bubble created by the laser may escape through the laceration into the adjoining tissue and nerve structures. Another disadvantage is that needle punctures that penetrate the catheter wall may damage the integrity of the catheter and/or the optical fiber. Finally, multiple injections require the use of multiple needles and other accessories such as gauze pads and syringes. The medical staff performing the procedure is thus at an increased risk of accidental needle sticks and the potential health hazards associated with unintentional exposure to contaminated blood and other body fluids.

Therefore, it is desirable to provide an improved device and method which delivers vaso-spasming and anesthetic fluids and other procedural drugs quickly, completely and uniformly without multiple injections or multiple needle sticks. It is also desirable that the device and method prevent thermal damage to non-targeted adjacent tissues and nerve structures without requiring peri-venous injections along the entire length of the vein. Further, it is desirable provide such a method and device that reduce patient discomfort associated with needle sticks, decrease procedure time, and minimize postprocedure complications caused by multiple punctures.

SUMMARY OF THE DISCLOSURE

According to the principles of the present invention, a catheter device for treating a vascular disease is provided. The catheter device includes an energy delivery device such as an optical fiber for delivering laser energy and a catheter designed to be inserted into a blood vessel. The catheter lumen receives the energy delivery device and a fluid such as an anesthetic agent or vasoconstricting agent. According to the invention, a plurality of exits are disposed in the sidewall of the catheter. The exits are in communication with the catheter lumen and are used to administer the fluid into the blood vessel.

The catheter may have a single lumen through which both the energy delivery device and the fluid can be received. Alternatively, the catheter may have two separate lumens in which one lumen receives the energy delivery device and the other lumen receives the fluid.

In one aspect of the present invention, the exits of the catheter device are pressure responsive exits that are normally closed and are designed to open under a certain amount of pressure within the lumen.

By administering the fluids from within the catheter lumen, the present invention eliminates the need to make numerous external punctures to deliver tumescent injections. As a result, the invention provides substantial time and cost savings to a treating physician while reducing the trauma, pain and post-operative bruising of the patient.

BRIEF DESCRIPTION OF THE DRAWINGS

FIG. 4A depicts the catheter inserted over a guidewire within the enlarged vein.

FIG. 4B illustrates the catheter within the enlarged vein after guidewire removal.

FIG. 4C shows the optical fiber in the protected position within the catheter positioned within the enlarged vein.

FIG. 4D depicts the vein being constricted during the delivery of the drug through the pressure responsive outlets of the catheter with the optical fiber in the protected position.

FIG. 4E depicts the catheter with the optical fiber in the operating position within the constricted vein.

DETAILED DESCRIPTION OF THE INVENTION

Figure 1:
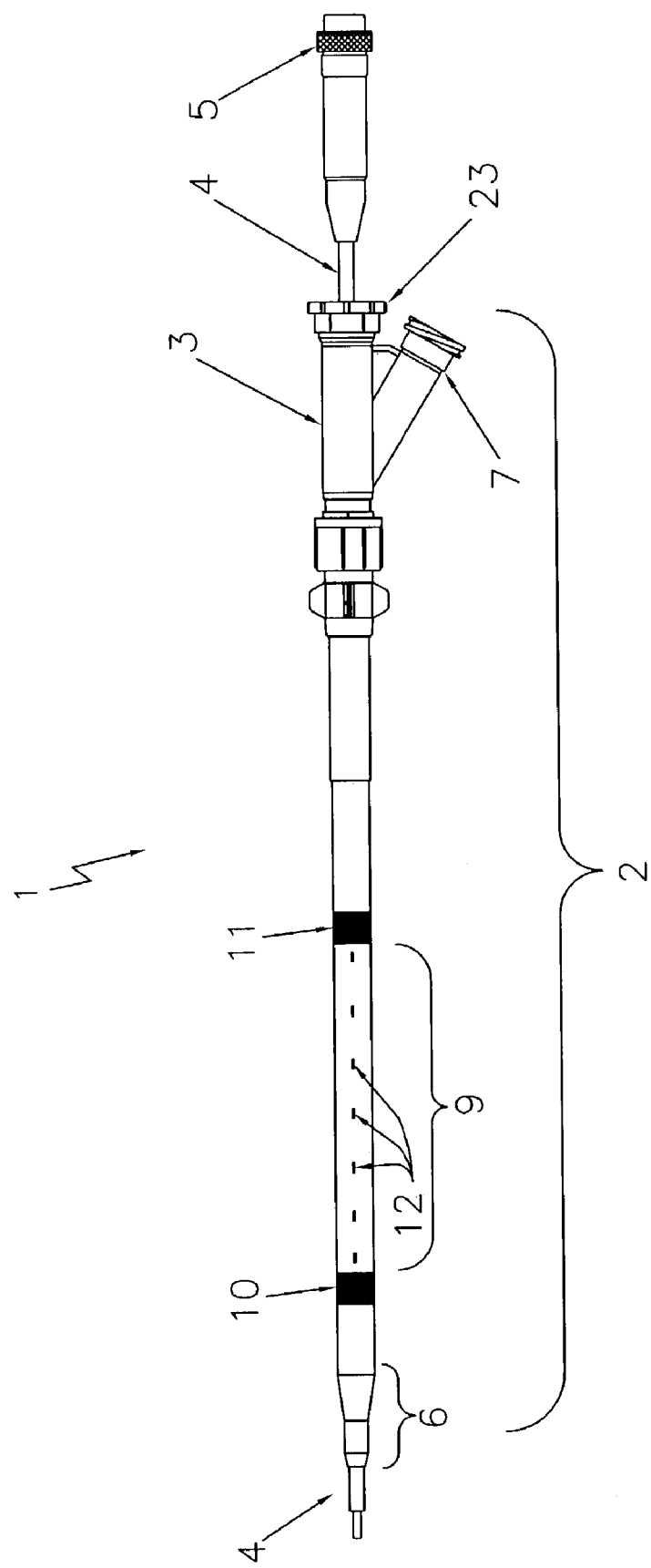
FIG. 1 illustrates an endovascular laser treatment device with an optical fiber assembled with an infusion catheter according to the present invention.

An endovascular laser treatment device 1 according to the present invention is illustrated in FIG. 1. It is to be noted that the device 1 is illustrated with only a laser optical fiber for purposes of clarity only. Other types of energy delivery source such as RF electrodes can also be used with the present invention.

Figure 2:
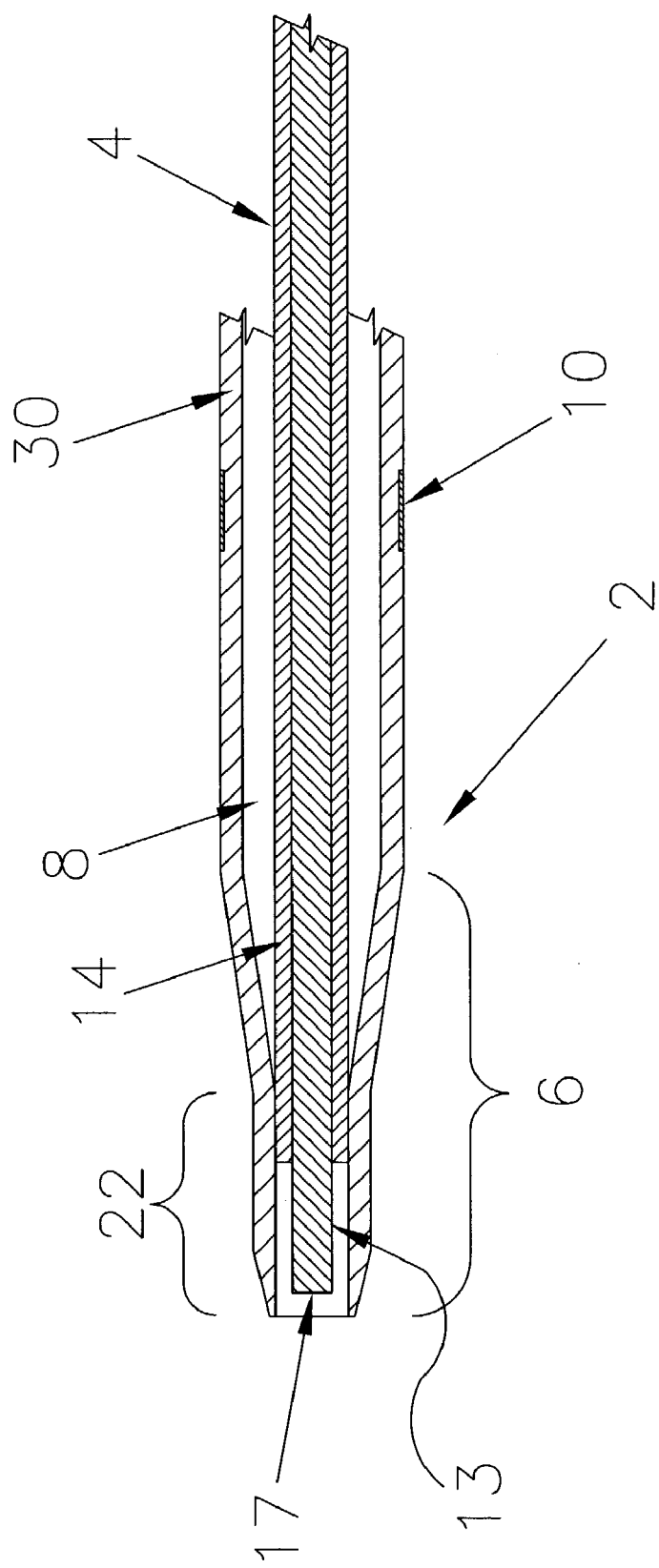
FIG. 2 is an enlarged view of the catheter/optical fiber tip area of FIG. 1 with the optical fiber in a protected position within the catheter.
Figure 3:
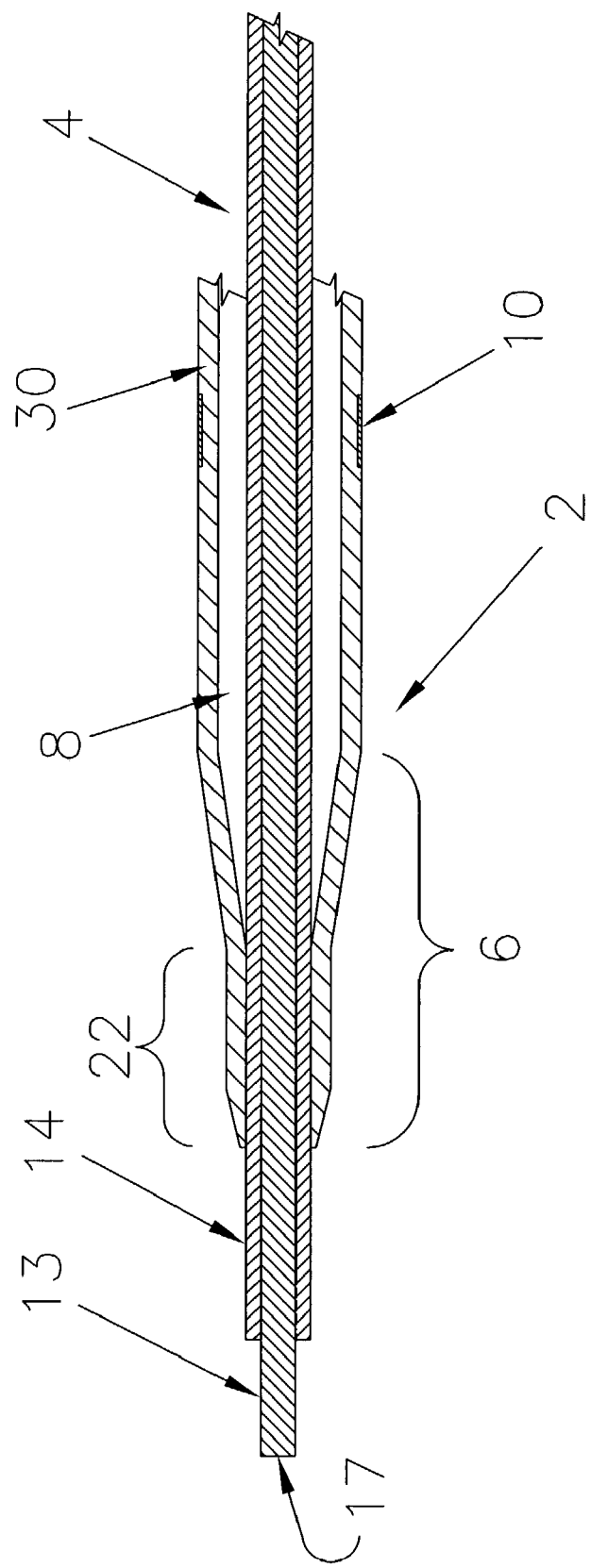
FIG. 3 is an enlarged view of the catheter/optical fiber tip area of FIG. 1 with the optical fiber tip in an operating position outside of the catheter.

The laser treatment device 1 includes an infusion catheter assembly 2 having a Y-connector 3, and an optical fiber 4 having a SMA connector 5. The catheter 2 is a tubular structure used to facilitate the passage of the optical fiber 4 within the cardiovascular system of a patient. Referring to FIGS. 1–3, the catheter 2 has a catheter tip section 6 with a through-lumen 8 for insertion and passage of the optical fiber 4. The catheter tip section 6 is defined by an occluding zone 22 shown in FIGS. 2–3. When the optical fiber 4 is inserted and advanced through the catheter lumen 8 into the occluding zone 22, the optical fiber 4 in contact with an inner wall of the occluding zone effectively seals the distal end hole of the catheter 2. The occluding zone 22 is dimensioned such that the optical fiber 4 will effectively seal the catheter end hole in both a protected position as shown in FIG. 2 and in an operating position as shown in FIG. 3. When the optical fiber is not advanced into the occluding zone 22, any fluid injected into the catheter is directed into the vein through the end hole of the catheter.

In the embodiment shown, the catheter 2 has a Y-connector 3 having a side arm port 7 for the injection of vaso-spasming fluid, saline or other drugs. The Y-connector 3 is also defined by through channel with a Touhy-Borst assembly 23. The Touhy-Borst assembly 23 is a gasket assembly used for holding and sealing around guidewires, fibers and other interventional devices inserted into the catheter lumen. By turning the locking mechanism of the Touhy-Borst assembly, the gasket within compresses or opens to allow insertion or sealing of the fiber 4 or other inserted device. When in the locked position, assembly 23 prevents the back-flow of blood or other fluids while holding the fiber 4 in position. In an alternative embodiment, a passive hemostasis valve may be used to prevent the backflow of blood.

The ends of the infusion segment 9 of the catheter 2 are marked with radiopaque markers 10 and 11. Marker 10 identifies the distal end of the infusion segment and marker 11 identifies the proximal end of the infusion segment. The infusion segment is typically about 50 cm long. According to the present invention, a plurality of pressure responsive exits such as pressure responsive slits 12 are uniformly formed in a sidewall 30 in the infusion segment 9 of the catheter 2. These pressure responsive slits 12 are in communication with the lumen of the catheter and are designed to open under a predetermined pressure, as described in U.S. Pat. No. 5,250,034, which is incorporated herein by reference. In one embodiment, there is a plurality of sets of slits with each slit being about 0.015 inches in length. Each set of slits includes four slits that are radially spaced from each other at about 90 degrees. Each set of slits is longitudinally spaced apart from other sets by about 0.5 cm along the infusion segment 9.

Alternatively, the exits 12 can be in the form of a plurality of orifices in the sidewall 30 within the infusion segment 9 of catheter. The orifices are in communication with the lumen 8 of the catheter and are designed to provide an exit path for fluid from the lumen 8 into the vein.

Fluid injected into the side arm port 7 advances through the annular space created between the optical fiber 4 and the sidewall 30 of the catheter 2. When the catheter end hole is occluded by the optical fiber 4, the injected fluid exits through the pressure responsive slits 12 uniformly along the infusion segment 9, so that the fluid such as anesthesia is distributed equally within the vein along the entire treatment area. The position of the optical fiber 4 within the catheter tip section 6 may be in either the protected position or operating position as respectively shown in FIGS. 2 and 3. As long as the optical fiber is positioned within the occluding zone 22 of the catheter 2, fluid flow is directed from the catheter 2 through the pressure responsive outlets 12 and into the vein.

The length of the infusion segment 9 may be up to 50 cm long to ensure adequate delivery of the therapeutic fluid along the diseased vein segment with a single injection. Although uniform drug delivery is accomplished with the design of the pressure responsive slits, standard sidewall orifices will provide adequate drug delivery throughout the diseased segment of the vein. As long as the end hole of the catheter 2 is occluded by the energy delivery device, sufficient drug volume will be delivered through the sidewall orifices to ensure therapeutic effect throughout the infusion segment 9.

The optical fiber 4, depicted in detail in FIG. 2 and FIG. 3, is a standard laser fiber composed of a thin filament of glass or similar material surrounded by a silica cladding 13. The purpose of the silica cladding 13 is to reflect laser energy back into the fiber as it travels the length of the fiber 4 allowing laser energy emission only through the fiber tip 17. A plastic, coaxially mounted protective jacket 14 surrounds the fiber cladding 13 to provide additional strength, protection from surface damage and isolation from moisture. The protective jacket 14 terminates approximately 4 mm from the distal tip of the fiber 4. As shown in FIGS. 2 and 3, the occluding zone 22 of the catheter tip 6 is dimensioned to ensure that when in the protected position (see FIG. 2), the protective jacket 14 remains within the occluding zone 22 ensuring occlusion of the catheter 2 end hole.

The optical fiber 4 including the cladding 13 is typically between 400 and 1000 microns in diameter, and preferably about 600 microns. The optical fiber 4 including the cladding 13 and the protective jacket 14 is between 870 and 1470 microns, and preferably about 1070 microns. The end of the fiber 4 terminates at the energy-emitting end 17, which is typically a flat-faced surface of the fiber tip 17. Alternatively, the fiber tip face 17 may be radiused or have a non-flat surface. At the proximal end, the fiber 4 is attached to a connector 5 such as a standard SMA connector. The SMA connector 5 connects the fiber 4 to a laser energy source (not shown).

A method of using the endovascular laser device 1 in treating varicose veins will now be described with reference to FIGS. 4A–4E. The treatment procedure begins with the standard pre-operative preparation of the patient as is well known in the thermal energy treatment art. The patient is examined with ultrasound to identify and locate the source of venous reflux, typically the greater saphenous vein. Treatment is not necessarily limited to the greater saphenous vein; diseased segments of the lesser saphenous vein and other veins may be treated using endovenous laser or RF procedures. The saphenofemoral junction and any anatomical variations of the venous system are also identified during pre-treatment ultrasound After the ultrasound examination, the patient's leg is draped and cleansed in preparation for the procedure.

With prior art methods, the patient's diseased venous segments are marked on the skin surface. Typically, ultrasound guidance is used to map the greater saphenous vein from the sapheno-femoral junction to the popliteal area. The physician marks the route of the vein with a marker under ultrasound guidance. The purpose of this mapping is to provide a visual identifying line for the physician to follow when injecting peri-venous tumescent anesthesia along the length of the diseased vein. As persons of ordinary skill in the art can appreciate, mapping of the vein is a very time-consuming step for the physician. As will be explained in more detail later herein, the present invention advantageously eliminates the conventional mapping step from the treatment procedure. There is no need to pre-map the patient's venous pathway since the anesthetic or vasospasming drug will be administered intra-venously without punctures in a single injection through the catheter.

After the patient has been prepped, the greater saphenous vein 15 is accessed using a standard Seldinger technique. A guide wire 16 is advanced into the vein 15, and then the catheter 2 is fed over the guidewire 16 (FIG. 4A) and advanced to 1 to 2 centimeters below the sapheno-femoral junction. Position of the catheter 2 is then verified and adjusted if necessary using ultrasound. Once correct positioning is confirmed, the guidewire 16 is removed leaving the catheter 2 in place within the vein 15 as depicted in FIG. 4B.

Figure 4:
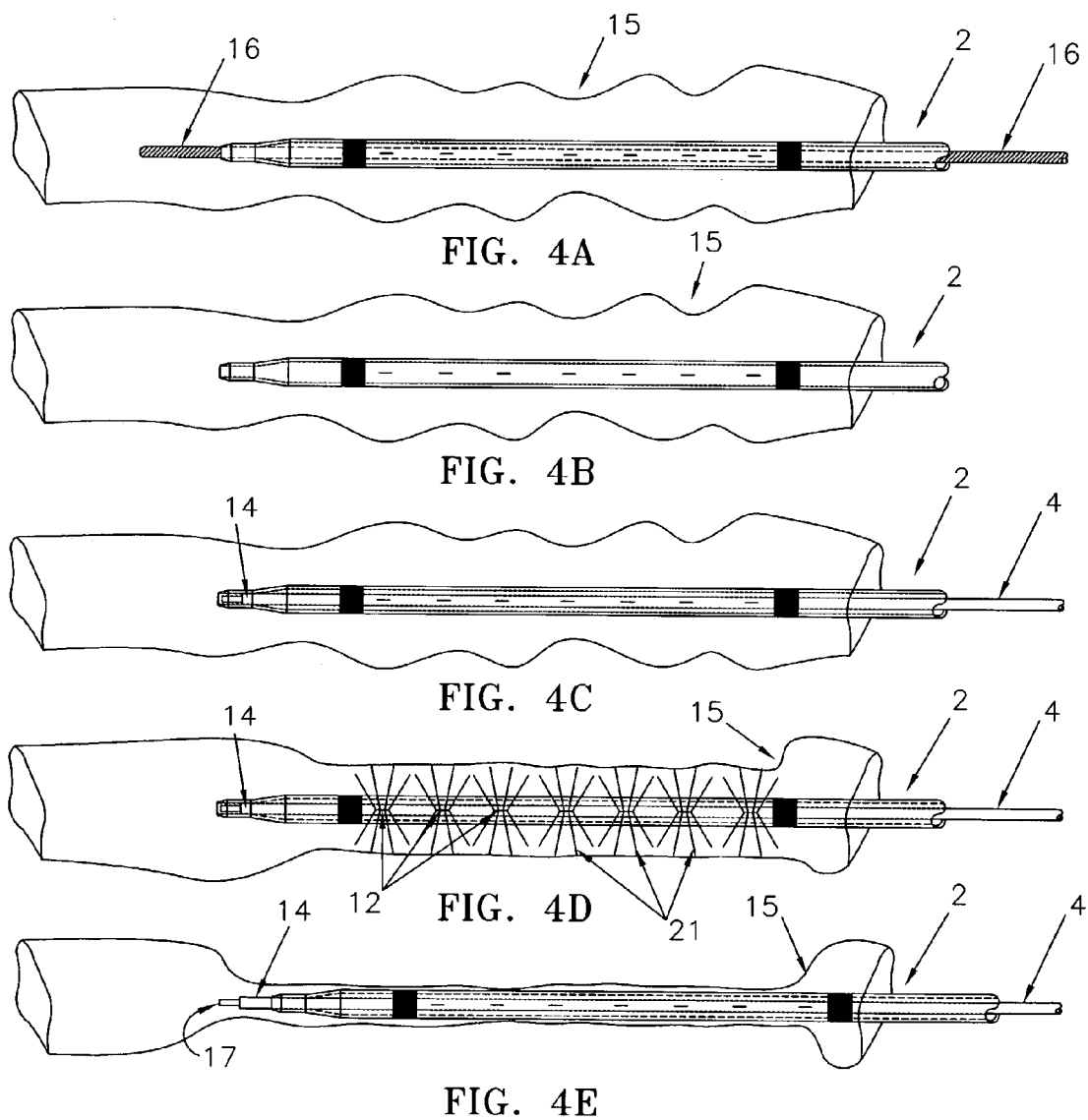
FIGS. 4A–4E illustrate the method of drug delivery using the device of FIG. 1.

As shown in FIG. 4C, the distal tip of the optical fiber 4 is then inserted into the catheter Y-connector 3 (not shown) and advanced until the fiber jacket 14 of optical fiber 4 is positioned within the occluding zone 22 of the catheter 2 in the protective position (FIG. 2). After positioning, the Touhy-Borst assembly 23 is turned to lock the optical fiber in place in the protected position. In that state, the catheter 2 end hole is effectively occluded by the fiber jacket 14.

Once the catheter 2 and optical fiber 4 are positioned, infusion of one or more drugs is performed. As discussed earlier in the background section, the conventional drug infusion process involves making 10 to 20 needle punctures to deliver 10 to 20 perivenous injections under ultrasound guidance. For each injection, the needle must be positioned accurately using ultrasound guidance. Typically, between 3–10 cc of tumescent fluid are injected at each puncture site. Up to 200 cc of drug may be required to effectively prepare the vein and patient for the procedure. The injections can be painful to the patient, leave multiple puncture wounds and may increase bruising and post-procedure complications. The injections also may compromise the integrity of the delivery system due to penetration of a catheter wall by inaccurate needle sticks.

According to the principles of the present invention, however, the therapeutic fluid is administered from within the catheter without the need to make any punctures. Specifically, using a standard syringe connected to the side arm port 7 of the catheter Y-connector 3 (FIG. 1), the drug is infused into the catheter 1 in a single bolus. Under low, steady pressure, the fluid advances into the annular fluid passageway formed between the optical fiber 4 and catheter 2 sidewall 30. Occlusion of the catheter end hole by the optic fiber jacket 14 causes the drug 21 to exit from the slits 12 in the sidewall 30 of the catheter into the vein 15, as shown in FIG. 4D. The drug 21 does not exit from the end hole of the catheter 2 because it is effectively occluded by the optical fiber jacket 14. Drug can be delivered with the laser in the protected position as shown in FIG. 2 or in the operating position as shown in FIG. 3, based on the treating physician's preference.

The fluid 21 being infused into the vein has vaso-spasming and anesthetic characteristics. The induced spasm in turn causes the vein to constrict. For example, fluid such as Lidocaine, hypertonic saline and sclerosing agents may be injected to induce vaso-spasms. Sclerosing agents serve an additional function of causing vascular fibrosis by acting upon the vessel wall. Typically a solution of 1% Sotradecol or Polidocanol is administered to the vein.

Anesthetics are used for an additional purpose of decreasing pain during the procedure. Lidocaine is typically used to alleviate patient pain. Typically a mixture of 10–30 cc of 5% lidocaine with epinephrine is used. Alternatively, Marcaine, a longeracting form of lidocaine, can be injected through the side arm port 7.

The vaso-spasming characteristics of lidocaine and epinephrine act upon the inner wall of the diseased vein causing it to spasm and constrict around the endovascular treatment device 1. Referring to FIG. 4E, the enlarged vein diameter is significantly reduced in reaction to the delivery of the drug to the inner vein wall. Complete spasm of the vein is desirable to reduce the size of the vein diameter prior to laser energy delivery. As the vein spasms and constricts, the distance between the vein and the nerve increases. The extra distance provides a barrier to prevent non-targeted thermal damage to the nerve during laser energy delivery.

The design and uniform spacing of the pressure responsive slits 12 ensure uniform and rapid delivery of the vaso-spasming and/or anesthetic fluid along the entire infusion segment 9 of the catheter 2. Accordingly, the vein 15 can be treated with a single fluid injection. This aspect of the invention provides substantial time and cost savings to the treating physician while reducing the trauma, pain and post-operative bruising of the patient.

Typically, an endovenous laser procedure may take 45 to 120 minutes including prep and post-procedure steps. Of that time, approximately 10 to 20 minutes are allocated to completely anesthetize the entire vein segment being treated. With the treatment method described in this invention, however, the administration of anesthetic and/or vasospasming fluid is reduced to literally several seconds.

With the present invention, patient side effects and complications from multiple needle punctures are avoided. Patient pain associated with the needle puncture and injection of fluid into tissue is completely eliminated with the endovascular laser technique described herein. Post-procedure bandaging of the patient's leg is simplified because of the absence of puncture wounds.

In addition, the total amount of lidocaine or like drug injected using the catheter assembly of the present invention is significantly less than the amount required for perivenous injections. Because the drug is being delivered directly to the inner vein wall, less drug is required. Typically, only 10–30 cc of anesthesia is required when delivered intravenously compared with 100–200 cc tumescent fluid when delivered perivenously.

Figure 6:
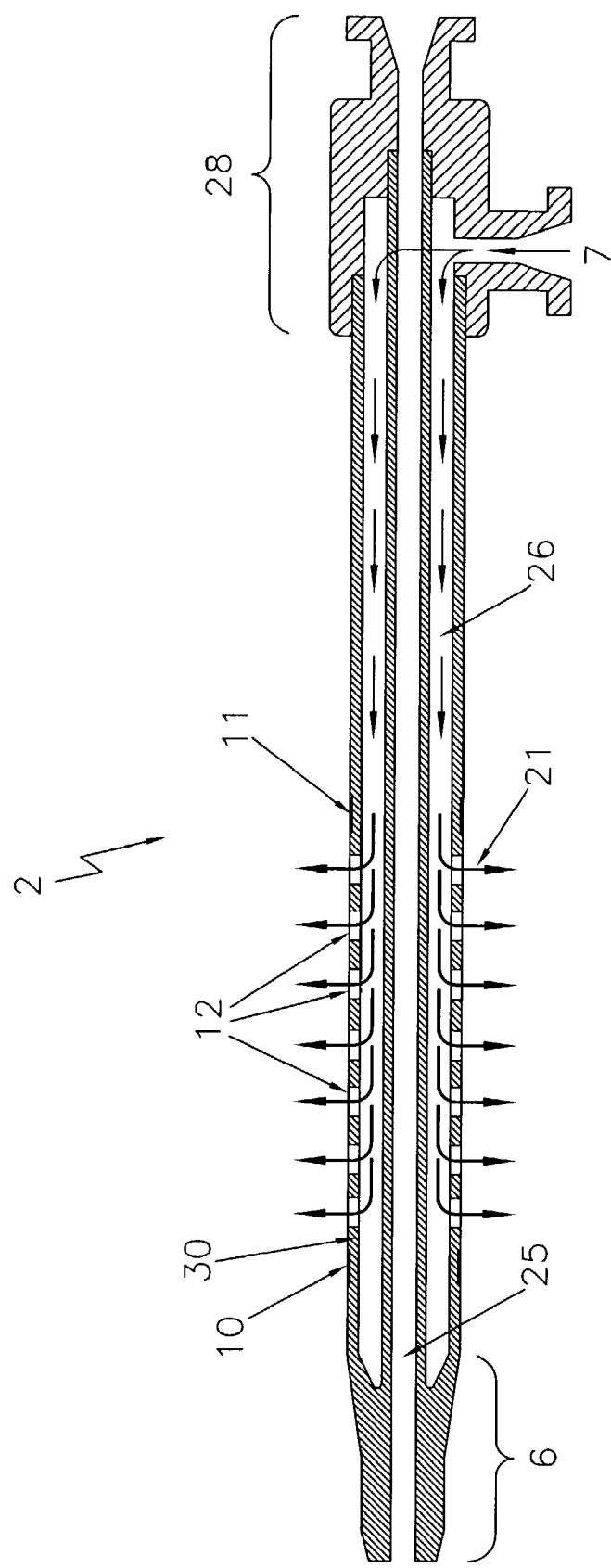
FIG. 6 is a sectional view of an alternative embodiment of a catheter with a co-axial lumen.
Figure 7:
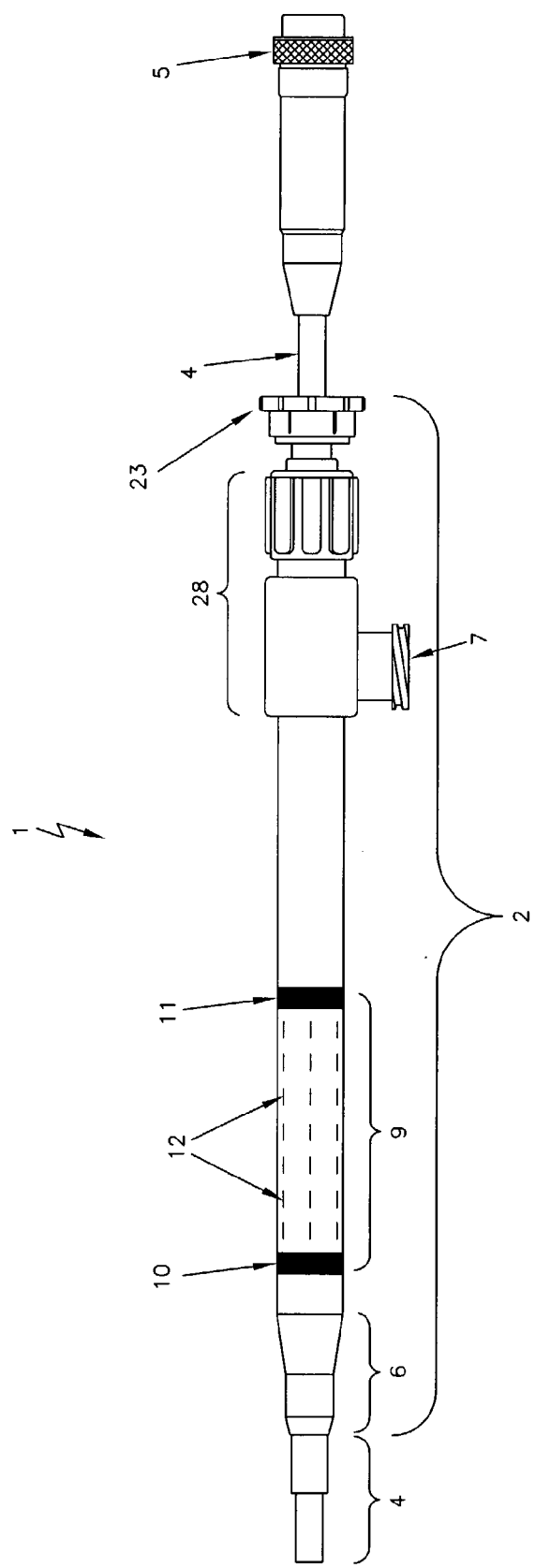
FIG. 7 is a plan view of the catheter of FIG. 6 assembled with the optical fiber.

An alternative embodiment of the catheter 2 is depicted in FIG. 6. The catheter 2 is comprised of an inner through lumen 25 and an outer, coaxial lumen 26 for fluid flow. At the proximal end, the catheter 2 is defined by a T-connector 28 having a side arm port 7 for the injection of vaso-spasming agents, saline or other drugs. The T-connector 28 is also defined by through channel with a Touhy-Borst assembly 23 as depicted in FIG. 7. Fluid is infused through the side port 7 into the annual space of the coaxial lumen 26. The coaxial lumen 26 is an annular lumen and surrounds the inner through lumen 25. When injected through the side port 7, the fluid 21 advances through the annular fluid passageway 26 exiting through the pressure responsive exits 12 into the vessel lumen. In this embodiment, fluid can be administered intravenously without occlusion of the catheter 2 end hole because of the coaxial design. Accordingly, vasoconstricting and anesthetic drugs can be injected into the catheter 2 prior to inserting the fiber optic 4 into the inner through lumen 25 of the catheter 2.

Alternatively, drugs can be administered through the catheter pressure responsive exits 12 with the fiber optic 4 positioned within the catheter lumen 26 in the protected or operating position. As shown in FIG. 7, the optical fiber 4 is inserted and advanced into the through lumen 25 of catheter 2. By turning the locking mechanism of the TouhyBorst assembly, the gasket within compresses or opens allowing insertion or sealing of the fiber 4 or other inserted device. When in the locked position, assembly 23 prevents the back-flow of blood or other fluids while holding the fiber 4 in position. In an alternative embodiment, a passive hemostasis valve may be used to prevent the backflow of blood.

After the anesthetic and/or vaso-spasming fluid has been delivered to the vein, the patient is ready for the delivery of laser energy to the diseased vein. The delivery system is repositioned from the protected position as shown in FIGS. 2 and 4D to the operating position as shown in FIGS. 3 and 4E to expose the laser optical fiber tip 17 of optical fiber 4. Typically, the catheter 2 is retracted approximately 2–4 cm while the laser fiber 4 is held steady to expose the fiber 4 energy emitting end 17 as shown in FIG. 4E. The endovascular laser treatment device 1 is now ready for the delivery of laser energy to the diseased vein segment.

Figure 5:
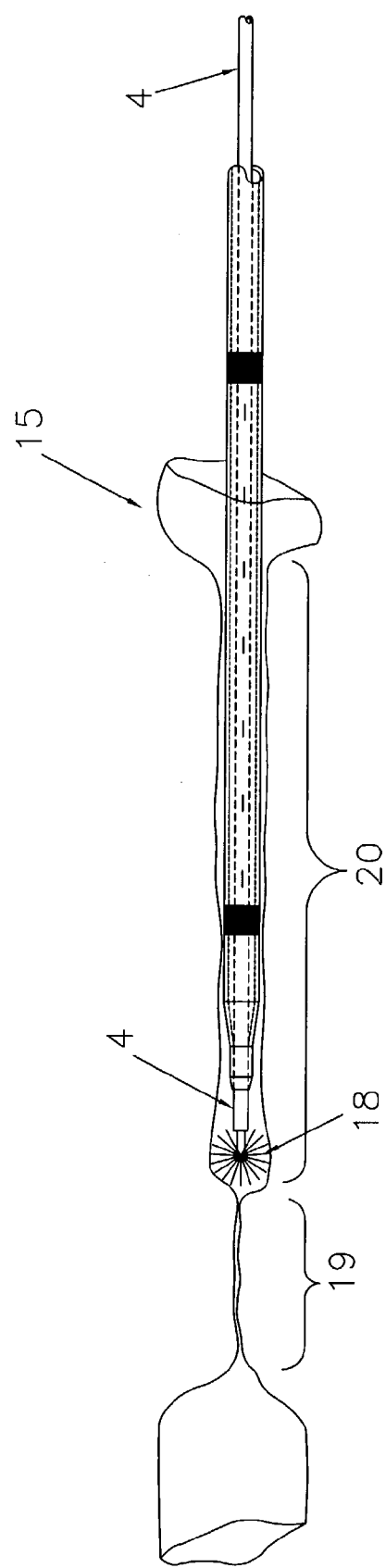
FIG. 5 illustrates the endovascular laser treatment device of FIG. 1 with the optical fiber delivering laser energy to the inner wall of the diseased vein while the catheter is being retracted through the vein.

The laser generator (not shown) is activated and the catheter 2/fiber 4 assembly is slowly withdrawn as a single unit through the vein, preferably at a rate of 1–3 millimeters per second. FIG. 5 depicts the catheter 2 and laser fiber 4 as the combined assembly is being pulled back down the course of the vein 15. As shown in FIG. 3, laser energy 18 is delivered to the inner wall of the vein as the catheter 2 is withdrawn. The laser energy 18 produces localized thermal injury to the endothelium and vein wall causing further reduction in the diameter of the vein and ultimately occlusion of the vein. Specifically, the thermal energy contacts the blood causing hot bubbles of gas to be created. The gas bubbles transfer the thermal energy to the vein wall, causing cell necrosis and eventual vein collapse.

In FIG. 5, section 19 of the diseased vein segment 15 has been treated with laser energy and is permanently occluded. Section 20 of the diseased vein segment 15 has not been exposed to laser energy and thus remains open but constricted. After the entire vein segment 15 has been treated, the thermally damaged vessel becomes occluded and can no longer support blood flow.

The procedure for treating the varicose vein is considered to be complete when the desired length of the greater saphenous vein or other vein has been exposed to laser energy. Normally, the laser generator is turned off when the fiber tip 17 is approximately 3 centimeters from the access site. The fiber 4/catheter 2 assembly is then removed from the body as a single unit.

While certain novel features of this invention have been shown and described above, the present invention may be embodied in other specific forms without departing from the spirit or essential characteristics of the invention. The described embodiments are to be considered in all respects only as illustrative and not as restrictive. Various omissions, modifications, substitutions and changes in the forms and details of the device illustrated and in its operation can be made by those skilled in the art without departing in any way from the spirit of the present invention.

What is claimed is:

1. A catheter device for treating a vascular disease comprising:
   an energy delivery device having an energy delivery portion including an energy emission tip; and
   a catheter having an end hole at its distal end and being operable to be inserted into a blood vessel and including:
      at least one lumen through which the energy delivery portion and a fluid is received, the at least one lumen being coaxial with a longitudinal axis of the catheter; and
      a plurality of exits disposed in the sidewall of the catheter and being in communication with the at least one lumen for administration of the fluid into the blood vessel, the plurality of exits being longitudinally spaced from the energy delivery portion;
   wherein the energy delivery device has a protected position in which the energy emission tip is positioned within the at least one lumen and an operating position in which the energy emission tip extends outside and distally of the end hole;
   wherein the energy delivery portion occludes the end hole to prevent the fluid from exiting through the end hole in both the operating position and the protected position.

2. The catheter device according to claim 1 wherein the at least one lumen constitutes a single lumen through which both the energy delivery device and the fluid are received.

3. The catheter device according to claim 1 wherein the exits include a plurality of pressure responsive exits.

4. The catheter device according to claim 1 wherein:
   the at least one lumen includes a first lumen through which the energy delivery device is received and a second lumen through which the fluid is received;
   the first and second lumens are separate lumens; and
   the plurality of exits are in communication with the second lumen.

5. The catheter device according to claim 4 wherein the second lumen is an annular lumen that surrounds the first lumen.

6. The catheter device according to claim 1 wherein the fluid received by the at least one lumen includes an anesthetic agent or vasoconstricting agent or both.

7. The catheter device according to claim 1 wherein each exit includes a normally closed pressure responsive exit that is designed to open in response to an internal fluid pressure in excess of a predetermined pressure level.

8. The catheter device according to claim 1 wherein the energy delivery device includes an optical fiber that delivers laser energy at a target vessel site.

9. The catheter device according to claim 8 wherein the fluid received by the at least one lumen includes an anesthetic agent or vasoconstricting agent or both.

10. The catheter device according to claim 9 wherein the exits include a plurality of pressure responsive exits.

11. The catheter device according to claim 1 wherein the energy delivery device is a radio frequency (RF) electrode that delivers RF energy at a target vessel site.

12. A catheter device with a laser energy delivery device for treating a venous disease, comprising:
   an optical fiber having an energy delivery portion including an energy emission tip capable of delivering laser thermal energy to a target area to be treated; and
   a catheter having an end hole at its distal end and being operable to be inserted into a vein and including:
      at least one lumen through which the optical fiber and fluid are received, the at least one lumen being coaxial with a longitudinal axis of the catheter; and
      a plurality of exits disposed in the sidewall of the catheter and being in communication with the at least one lumen for administration of the fluid into the vein, the plurality of exits being longitudinally spaced from the energy delivery portion;
   wherein the optical fiber has a protected position in which the energy emission tip is positioned within the at least one lumen and an operating position in which the energy emission tip extends outside and distally of the end hole;
   wherein the energy delivery portion occludes the end hole to prevent the fluid from exiting through the end hole in both the operating position and the protected position.

13. The catheter device according to claim 12 wherein:
   the at least one lumen includes a first lumen through which the optical fiber is received and a second lumen through which the fluid is received;
   the first and second lumens are separate lumens that are in spaced relation to each other; and
   the plurality of exits are in communication with the second lumen.

14. The catheter device according to claim 12 wherein the exits include a plurality of pressure responsive exits.

15. The catheter device according to claim 12 wherein each exit includes a normally closed pressure responsive exit that is designed to open in response to an internal fluid pressure in excess of a predetermined pressure level.

16. A catheter device with a laser energy delivery device for treating varicose veins, comprising:
- an optical fiber having an energy delivery portion including an energy emission tip capable of delivering thermal laser energy to a target area to be treated; and
- a catheter having an end hole at its distal end and being operable to be inserted into a varicose vein and including:
  - at least one lumen through which the optical fiber and a fluid are received, the fluid containing a vasoconstricting agent or anesthetic agent, or both, the at least one lumen being coaxial with a longitudinal axis of the catheter; and
  - a plurality of exits disposed in the sidewall of the catheter and being in communication with the at least one lumen for administration of the fluid into the varicose vein, the plurality of exits being longitudinally spaced from the energy delivery portion;
- wherein the optical fiber has a protected position in which the energy emission tip is positioned within the at least one lumen and an operating position in which the energy emission tip extends outside and distally of the end hole;
- wherein the energy delivery portion occludes the end hole to prevent the fluid from exiting through the end hole in both the operating position and the protected position.

17. The catheter device according to claim 16 wherein:
- the at least one lumen includes a first lumen through which the optical fiber is received and a second lumen through which the fluid is received;
- the first and second lumens are separate lumens; and
- the plurality of exits are in communication with the second lumen.

18. The catheter device according to claim 17 wherein the exits include a plurality of pressure responsive exits.

19. A method of treating a vascular disease comprising:
- inserting into a vessel a catheter having at least one lumen and a plurality of exits disposed in the sidewall of the catheter;
- inserting an energy delivery device having an energy delivery portion into the at least one lumen of the catheter to position the energy delivery portion near a distal end of the catheter so as to occlude a distal end hole of the at least one lumen of the catheter;
- introducing a fluid into the at least one lumen of the catheter such that the fluid flows out of the at least one lumen into the vessel through the plurality of exits in the sidewall; and
- applying energy through the distal end of the energy delivery device to cause closure of a vessel portion being treated while the energy delivery portion is occluding the distal end hole of the catheter.

20. The method according to claim 19 wherein the at least one lumen is a single lumen through which both the energy delivery device and the fluid are received.

21. The method according to claim 19 wherein the at least one lumen includes two separate lumens.

22. The method according to claim 19 wherein the step of introducing a fluid includes introducing an anesthetic agent or vasoconstricting agent or both.

23. The method according to claim 19 wherein each exit includes a normally closed pressure responsive exit, and the step of introducing a fluid includes introducing the fluid under pressure at a level sufficient to open the exits.

24. The method according to claim 19 wherein the step of inserting an energy delivery device includes inserting an optical fiber that delivers laser energy at a target vessel site.

25. The method according to claim 24 wherein:
- the fluid received by the at least one lumen includes an anesthetic agent or vasoconstricting agent or both; and
- the exits include a plurality of pressure responsive exits.

26. The catheter device according to claim 1, wherein the at least one lumen of the catheter is adapted to receive a sclerosing agent.

27. The catheter device according to claim 12, wherein the at least one lumen of the catheter is adapted to receive a sclerosing agent.

28. The catheter device according to claim 16, wherein the at least one lumen of the catheter is adapted to receive a sclerosing agent.

29. The method according to claim 19, wherein the step of introducing a fluid includes introducing a sclerosing agent.

* * * * *